(12) United States Patent
Götte et al.

(10) Patent No.: US 7,699,793 B2
(45) Date of Patent: Apr. 20, 2010

(54) METHOD AND DEVICE FOR DETECTING AND LOCALISING AN IMPINGEMENT OF JOINT COMPONENTS (75) Inventors: Hubert Götte, München (DE); Martin Immerz, Gräfelfing (DE)

(73) Assignee: BrainLAB AG, Feldkirchen (DE)

( * ) Notice: Subject to any disclaimer, the term of this patent is extended or adjusted under 35 U.S.C. 154(b) by 25 days.

(21) Appl. No.: 11/683,095

(22) Filed: Mar. 7, 2007

(65) Prior Publication Data
US 2007/0213643 A1 Sep. 13, 2007

Related U.S. Application Data (60) Provisional application No. 60/743,748, filed on Mar. 24, 2006.

(30) Foreign Application Priority Data
Mar. 7, 2006 (EP) ................... 06004601

(51) Int. Cl.
A61B 5/103 (2006.01)
A61B 5/117 (2006.01)
G01C 9/00 (2006.01)
G01C 17/00 (2006.01)
G01C 19/00 (2006.01)
(52) U.S. Cl. ................. 600/595; 600/587; 702/150
(58) Field of Classification Search ........ 600/595, 600/587; 702/150; 700/245
See application file for complete search history.

(56) References Cited

U.S. PATENT DOCUMENTS

| 6,205,411 B1 * | 3/2001 | DiGioia et al. ............ 703/11 |
| 6,708,142 B1 | 3/2004 | Baillot et al. |
| 7,001,346 B2 * | 2/2006 | White ....................... 600/587 |
| 2003/0100953 A1 * | 5/2003 | Rosa et al. ............... 623/20.3 |
| 2004/0181149 A1 * | 9/2004 | Langlotz et al. .......... 600/431 |
| 2005/0113720 A1 | 5/2005 | Cinquin et al. |
| 2005/0222574 A1 | 10/2005 | Giordano et al. |

(Continued)

FOREIGN PATENT DOCUMENTS

| DE | 100 62 580 | 7/2002 |
| WO | 02/02028 | 1/2002 |

OTHER PUBLICATIONS

Yanai, Toshimasa and Hay, James. "Shoulder impingement in front-crawl swimming: II. analysis of stroking technique." Medicine and Science in Sports and Exercise., vol. 32, No. 1, pp. 30-40, 2000.*
Moctezuma et al., "Robotic Surgery and Planning for Corrective Femur Osteotomy", Sep. 12, 1994.

(Continued)

*Primary Examiner*—Max Hindenburg
*Assistant Examiner*—Sean P Dougherty
(74) *Attorney, Agent, or Firm*—Renner, Otto, Boisselle, Sklar, LLP (57) ABSTRACT

A device and method for detecting an impingement of joint components of a joint includes detecting a spatial position of each joint component during a relative movement of the joint components; calculating an instantaneous center point of rotation or an instantaneous axis of rotation from the detected spatial positions of the joint components; when one joint component moves relative to the other joint component, establishing whether the calculated instantaneous center point of rotation moves within a first expectation range or whether the calculated instantaneous axis of rotation moves within a second expectation range; and establishing that there is an impingement of the joint components when at least one of the calculated instantaneous center point of rotation or the calculated instantaneous axis of rotation leaves or exits the respective expectation range.

21 Claims, 6 Drawing Sheets

Centre of rotation during the impingement

U.S. PATENT DOCUMENTS

2005/0251065 A1 11/2005 Henning et al.
2006/0095047 A1* 5/2006 de la Barrera ............... 606/102
2006/0189864 A1* 8/2006 Paradis et al. ............... 600/407
2006/0264731 A1* 11/2006 Murphy ..................... 600/407

OTHER PUBLICATIONS

European Search Report for corresponding Application No. EP 06 00 4601 dated Sep. 13, 2006.

* cited by examiner

FIG. 1a

Movement of the instantaneous axis of rotation of the femur over a bending range of motion

FIG. 1d

Movement of the femoral centre of rotation along the physiologically or kinematically defined path, as seen in the sagittal projection

FIG. 1b

The axes of rotation lie in a curved plane and intersect the sagittal projection plane

FIG. 1c

The intersecting points (centres of rotation) run along a physiologically or kinematically defined path, e.g. the moving centrode curve

FIG. 2a

Movement of the centre of rotation of a wheel

FIG. 2b

Centre of rotation of a rocker

FIG. 3a
Centre of rotation during the impingement

FIG. 3b

The axes of rotation within the range of motion lie in a curved plane. When an impingement occurs, these then jump and can form a bundle of lines intersecting in the region of the impingement (arrow). In this example, the impingement occurs behind the sagittal plane shown. In the sagittal projection, the centres of rotation move away from the physiologically defined path and collect in the posterior distal corner of the sagittal projection plane.

Centres of rotation during normal bending remain near to a defined path or range, until an impingement occurs. During the impingement, the centres of rotation deviate significantly from the defined path and collect around the region of the impingement in the sagittal projection.

FIG. 4

Two transformations T1 and T2 describe the position of the femoral co-ordinate system KF before (KF1) and after (KF2) a change in position during a finite bending step with respect to the tibial co-ordinate system KT. The helical axis parameters (the bending angle θ, the point s on the axis and the direction vector n with respect to the tibial co-ordinate system KT) can be obtained from these matrices. The matrices can be obtained from tracking the reference arrays on the femur and tibia.

METHOD AND DEVICE FOR DETECTING AND LOCALISING AN IMPINGEMENT OF JOINT COMPONENTS

RELATED APPLICATION DATA

This application claims priority of U.S. Provisional Application No. 60/743,748 filed on Mar. 24, 2006, which is incorporated herein by reference in its entirety.

FIELD OF THE INVENTION

The present invention relates to a method and device for detecting and localizing a location of an impingement of joint components of a joint, such as, for example, a knee, elbow or hip joint.

BACKGROUND OF THE INVENTION

In surgery in the region of an anatomical joint, such as during and after implantation of an artificial joint, care should be taken that the joint moves as freely as possible. For example, the joint should pivot and/or rotate without one joint component (artificially inserted as an implant) nudging or abutting another joint component during normal joint movement so as to jam when the joint is further moved. Such interference can lead to excessive wear and/or functional impairment of the joint.

According to known surgical methods, the condyles, as a precaution, should be trimmed anteriorly and posteriorly, as for example described in "The Oxford Phase 3, Unicompartmental Knee, Manual of the Surgical Procedure" published by Biomet Merck, "LCS Universal Kniesystem, OP-Technik" [LCS Universal Knee System, Operative Technique] published by DePuy, or "The M/G Unicompartmental Knee" published by Zimmer.

In order to detect an impingement, a method referred to as HIP ROM (range of motion) is known that can be implemented using a surgical navigation system, such as marketed by BrainLAB AG under the trade name Vector-Vision hip software. Marker arrays, for example, can be attached to each of the pelvis and the femur and can be tracked by a camera system. Then, after pivoting the hip joint about its center point, the coordinates of the pivoting point can be stored with respect to the pelvis and the femur. Since the hip joint can be regarded as a ball joint, during movement of the joint within its normal functional range, the two points coincide in the coordinate system of the camera. If, however, jamming occurs and a joint component is dislocated, for example, due to jamming, then these two points may deviate from each other. This deviation can be detected by software, although it is not possible to localize the jamming point or bearing point of the joints.

US 2005/0,113,720 A1, the contents of which is incorporated by reference in its entirety, discloses a method for determining the center point of rotation of a bone in a rotary joint, such as for example a femur in the ilium. DE 100 62 580 A1, which also is incorporated by reference in its entirety, discloses how the mechanical axis of a femur may be determined.

In general terms, the positions of joint components or bones can be detected, for example, by marker arrays or reference stars attached to the bones. The positions also can be detected by elements directly or indirectly connected to the bones, such as markers which can be localized, for example.

SUMMARY OF THE INVENTION

In a method for detecting an impingement of joint components of an anatomical joint (e.g., a hip joint, shoulder joint, elbow joint, or in the case of the knee joint, an impingement of the femur and tibia with or without artificial joints or joint parts), a spatial position of each joint component is detected, wherein the joint components are moved relative to each other so as to enable calculation of a location of an instantaneous axis of rotation from the changing relative spatial position of the joint components. In the case of a knee joint, for example, the axis of rotation can pass through the femur.

If the joint components impinge at a location during a continuous movement, instead of performing a roll-sliding typical for the knee joint, the (further) movement of the instantaneous axis of rotation or of an instantaneous center point of rotation leaves an expectation range. For example, the instantaneous axis of rotation of the knee joint will move out of its normal or defined working range or, in the event of a hard impingement, will abruptly change its position. In another case, by blocking further movement, the axis of rotation can remain within its working range but not move any further, thus no longer completely covering the normal or physiological working range of its movement. In particular cases, the newly ascertained axis of rotation will pass through the location at which the joint components impinge, such that the joint components no longer move relative to each other as defined by a joint connection, as desired, but rather tilt on the impingement or tilting line. This can lead to increased wear on the joint and to a joint component moving out of the placement necessary for functioning as a joint. Consequently, the joint can become disjoined or dislocated, also referred to as luxation. In the event of tilting, the instantaneous axes of rotation are concentrated in a certain environment near and around the tilting line, which can be detected as described herein.

An expectation range for the movement or further movement of an instantaneous axis of rotation or of an instantaneous center point of rotation can be determined or calculated in advance. This calculation can be used to predetermine a probable or supposed spatial movement of the instantaneous axis of rotation or of the instantaneous center point of rotation, for example, by a defined volume within which the instantaneous center point of rotation or the instantaneous axis of rotation moves. If the movement leaves this expectation range, then it is possible to establish that the joint components have impinged. Such a spatially defined expectation range also can be referred to as a global expectation range that predetermines a possible trajectory of movement over time, within certain boundaries (e.g., within a predetermined or defined volume) for the instantaneous axis of rotation or the instantaneous center point of rotation. Alternatively or in addition, it is equally possible to predetermine a local expectation range which, proceeding from a current position of the axis of rotation or the center point of rotation, predetermines the distance at which the next ascertained instantaneous axis of rotation or the next ascertained instantaneous center point of rotation can lie. For example, when the movement leaves the local expectation range, it is possible to establish that there is an impingement of joint components. It is then also possible that the movement leaves the local expectation range, but a newly ascertained center point of rotation or a newly ascertained axis of rotation still lies within the global expectation range. Irrespective of which expectation range is used, when the movement leaves the local expectation range, it is possible to establish that there is an impingement of the joint components. By means of a movement analysis, for example, such a local or global expectation range can be predetermined which represents an expectation with respect to the progress of a movement of two joint components relative to each other. The local or global expectation range also can define whether the movement progresses evenly, smoothly or constantly or whether there are unexpected events, e.g., jumps, such that an impingement of joint components can be deduced. The following embodiments, which relate for example to defined volumes or defined areas, predetermine global and/or local expectation ranges over these defined volumes or areas.

An expectation range also can be localized such that the instantaneous center point of rotation or the instantaneous axis of rotation lies inside or outside a predefined plausibility range (e.g., within a joint structure such as the femur) in order to rule out proceeding from a center point of rotation lying outside the femur.

An impingement of joint components of a joint can be detected by a) detecting a spatial position of each joint component during a relative movement of the joint components, b) calculating an instantaneous center point of rotation or an instantaneous axis of rotation from the detected spatial positions of the joint components, and c) when one joint component moves relative to the other joint component, establishing how the calculated center point of rotation moves along a curve. The curve may be calculated, for example, by interpolating over all the center points of rotation in the order they are passed. Alternatively, when one joint component moves relative to the other joint component, step c may include establishing how the calculated axis of rotation moves on a curved area that is calculated by interpolating over all the axes of rotation in the order they are passed.

If there are curved segments having a curvature above a predetermined boundary value or curved segments having a distance between adjacent center points of rotation above a predetermined boundary value or area segments having a curvature above a predetermined boundary value or area segments having a large distance between adjacent axes above a predetermined boundary value, it can be established that there is an impingement of the components. In the interpolation, an outlier treatment can be performed. The extent of the area, which can be calculated from the axes of rotation which extend ad infinitum, can also be limited by a predetermined volume having a finite extent.

Figure 6:
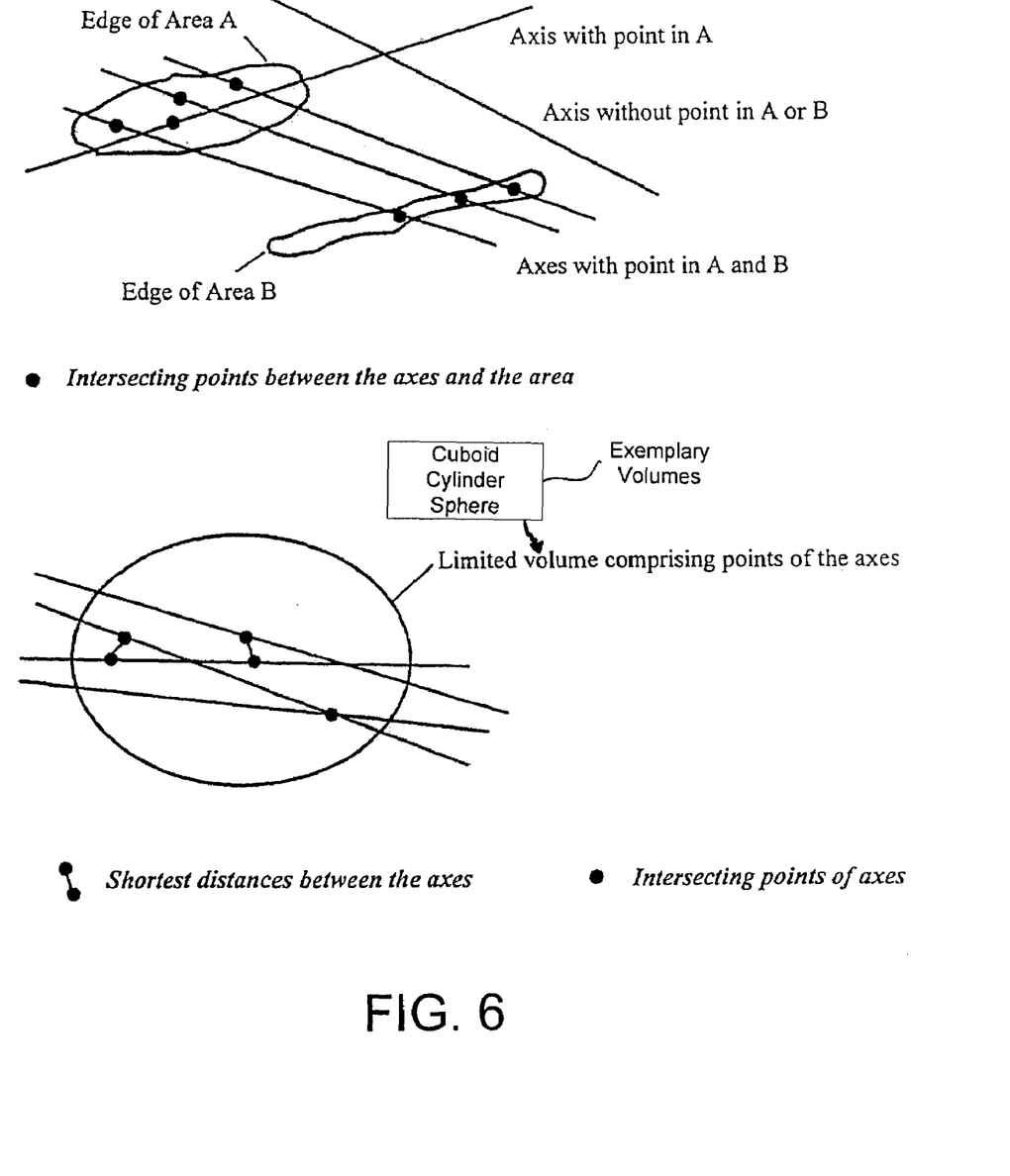
FIG. 6 illustrates the axes of rotation which intersect defined areas, and axes of rotation which intersect within a limited volume or, skewed, come closest to a point in accordance with the invention.

Thus, the presence of an impingement can be detected by monitoring the position of the instantaneous axis of rotation. In the case of a knee joint, for example, at least one of the following criteria can be monitored or detected:

whether the axis of rotation intersects one or more defined limited areas (see FIG. 6), wherein the defined area can also be the shell of a defined volume;

whether the axis of rotation moves, for example, in a volume previously defined or over a defined area;

whether the respective change in the position and orientation of the newly ascertained instantaneous axis of rotation lies within predetermined boundaries with respect to any previous determined axis of rotation;

whether the piercing points of the axes of rotation (i.e., the "centers of rotation") through the sagittal plane, for example in the middle of the knee, move within a defined range or along a defined curve (for example the so-called Gangpol or moving centrode curve) or in its vicinity;

whether the ascertained or instantaneous axis of rotation or the center of rotation completely or only partially covers a predetermined range; and/or whether the axes of rotation are situated at a defined minimum distance from the surfaces of the joint components, e.g., the tibia, femur or the inserted joint components on the tibia or femur.

If one or more of these criteria is not fulfilled, it is likely an impingement exists. The possible location of the impingement can be ascertained by examining the trajectory of the axes of rotation within a defined or delimited volume. When determining the most probable location, an iterative method, for example, can be applied, wherein a partial volume having a defined extent may be initially determined within the search volume. In the partial volume, the accumulation of intersection points and shortest distances between axes of rotation (see FIG. 6) can be determined. By moving the partial volume, the entire search volume can be covered. The partial volume having the greatest accumulation then can be taken as a new search volume and subjected to another, more exact search. If there is a common intersecting point, or a concentration of the axes of rotation or of their intersecting points in this volume, then the location of the impingement may be situated within this volume. It is then possible to test whether the ascertained location lies inside or outside a predefined plausibility range, in order to rule out incorrect locations. Thus, for example, if the rolling movement is blocked, the axes of rotation, providing they slide cleanly through the femur, will be concentrated within a narrow volume within the knee joint. However, this location will lie in the interior of the distal femur and cannot be the location of the impingement or obstruction, which lies on the edge of the bone structure or joint structure (in this case, the femur). Incorrect ascertation is ruled out by taking the interior of the femur into account as a predefined range. The usual range of motion of the axis of rotation of the knee joint, for example, can be gathered from the investigation by H. H. Wetz and H. A. C. Jacob, "Use of spatial motion of the femorotibial joint for the alignment of knee braces" in Orthopädie [Orthopaedics], 2001, 30: 196-207, Springer Publishing 2001.

In the example of a hip joint, normal functionality would be obtained if the ascertained instantaneous axes of rotation of the femur relative to the pelvis always intersect in a point or are concentrated in a particular range or volume. If the axis of rotation no longer intersects with the others in this point or no longer passes through the predetermined volume, the joint leaves its normal working range and there is an impingement of the joint components on the resulting tilting line, and this tilting line can be detected.

In the case of a hip joint, at least one of the following criteria can be monitored:

whether the axes of rotation always intersect in a common intersecting point or a defined volume around the intersecting point and/or pass through the defined volume; and/or whether the axes of rotation are situated at a defined minimum distance from the surfaces of the femur or tibia.

If one or more of these criteria is met, it is likely there is an impingement. The possible location of the impingement can be ascertained by examining the trajectory of the axes of rotation within a defined volume. When determining the most probable location, an iterative method, for example, can be applied, wherein a partial volume having a defined extent is initially determined within the search volume. In the partial volume, the accumulation of intersection points and shortest distances between axes of rotation (see FIG. 6) can be determined. By moving the partial volume, the entire search volume may be covered. The partial volume having the greatest accumulation then can be taken as a new search volume and subjected to another, more exact search. If there is a common intersecting point, a concentration of the axes of rotation or of their intersecting points, then the location of the impingement may be situated within this environment. As in the example of the knee joint, it is then tested whether the ascertained location lies inside or outside a predefined range so as to rule out incorrect locations.

Where a defined or predetermined area or range is mentioned in this application, this is also intended to mean areas in the form of a circle, an ellipse, a rectangle or other delimited outline, wherein the area, for example, can be defined by a specified distance from a point, such as, for example, a point of rotation (circle), or from a line or curve (e.g., the moving centrode curve or a bone outline). The distance, for example, can lie in the range of 0 to 10 cm and can measure 0 to 5 mm, 10 mm, 15 mm or 20 mm. The area also can be curved and/or composed of partial segments.

Where a defined or predetermined volume or spatial range is mentioned in this application, this is also intended to mean, for example, volumes in the form of a sphere, a cuboid, a cylinder or other delimited geometric body. The volume can be defined by a specified distance from a point, such as a point of rotation (sphere), or from an axis such as an axis of rotation (cylinder), or from a curve or line (e.g., the moving centrode curve or from a joint component or bone). The defined distance can lie in the range of 0 to 10 cm and can for example measure 0 to 5 mm, 10 mm, 15 mm or 20 mm. The volume can also be composed of a number of partial volumes.

Since anatomical joints such as, for example, the knee joint are not ideal ball joints, anatomical joints in most cases also do not have a fixed axis of rotation. Rather, the instantaneous axis of rotation moves with the movement of the joint or joint components, such that the instantaneous axis of rotation has to be localized by a so-called movement analysis, wherein the positions of the joint components are captured and the instantaneous axis of rotation can be calculated from the captured relative movement of the joint components.

Rodriguez has described a computational method for determining the underlying movement of rotation and translation from two spatial positions of a body; see Bisshopp, K. E.: "Rodriguez Formula and the Screw Matrix" in: Journal of Engineering for Industry, Transactions of the ASME (1969), pages 179-185. Panjabi has introduced this method into biomechanics; see Panjabi, M.; White, A. A.: "A Mathematical Approach for Three-Dimensional Analysis of the Mechanics of the Spine" in: Journal of biomechanics 4 (1971), No. 3, pages 203-211. Woltring proceeds from a transformation matrix to describing the orientation and position of the spatial positions; see Woltring, H. J.: "Representation and Calculation of 3-D Joint Movement" in: Human Movement Science 10 (1991), pages 603-616; Woltring, H. J.: "3-D Attitude Representation of Human Joints: A Standardization Proposal" in: Journal of Biomechanics 27 (1994), No. 12, pages 1399-1414; Woltring, H. J.; Huiskes, R.; Lange, A. de; Veldpaus, F. E.: "Finite Centroid and Helical Axis Estimation from Noisy Landmark Measurements in the Study of Human Joint Kinematics" in: Journal of Biomechanics 18 (1985), No. 5, pages 379-389.

Before a joint component is moved over the range of motion of the joint, a reference array such as a reference star, for example, provided with passive markers is preferably attached to the joint components (e.g., to the femur and the tibia). If these reference arrays are tracked using a tracking device, such as a tracking system that includes one or more cameras, for example, the instantaneous axes of rotation can be calculated from the tracked positional data.

Menschik, A.: "Biometrie—das Konstruktionsprinzip des Kniegelenks, des Hüftgelenks, der Beinlänge und der Körpergröße" [Biometrics—the constructional principle of the knee joint, hip joint, length of the leg and size of the body], Springer, 1987 et al. have described the knee joint as an überschlagene Viergelenkskette or estimated four-joint chain. When the femur is fixed (locked system), the tibia can be moved in the sagittal plane (moving system). The magnitude of the instantaneous centers of rotation generated by the tibia forms the locked centrode curve. If the tibia is fixed and the femur is moved, the instantaneous centers of rotation represent the moving centrode curve.

Figure 1A:
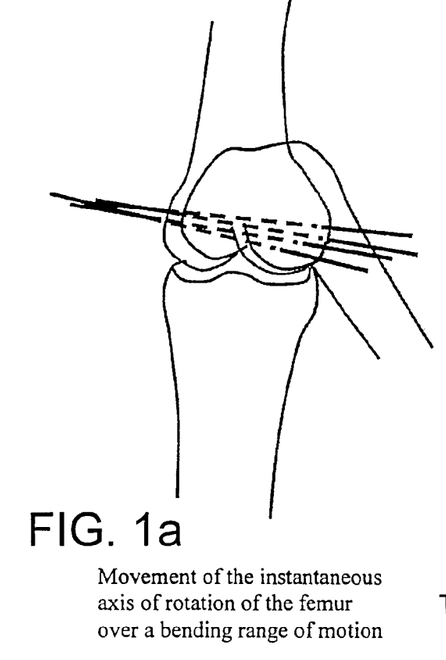
FIGS. 1a to 1d illustrate the change or shift in the instantaneous axes of rotation of a knee joint when bent.
Figure 1B:
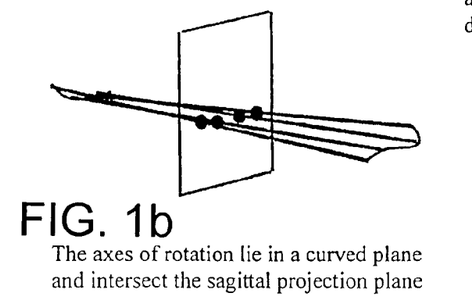
Figure 1C:
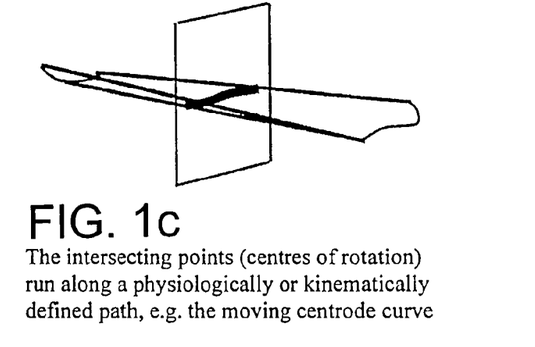
Figure 1D:
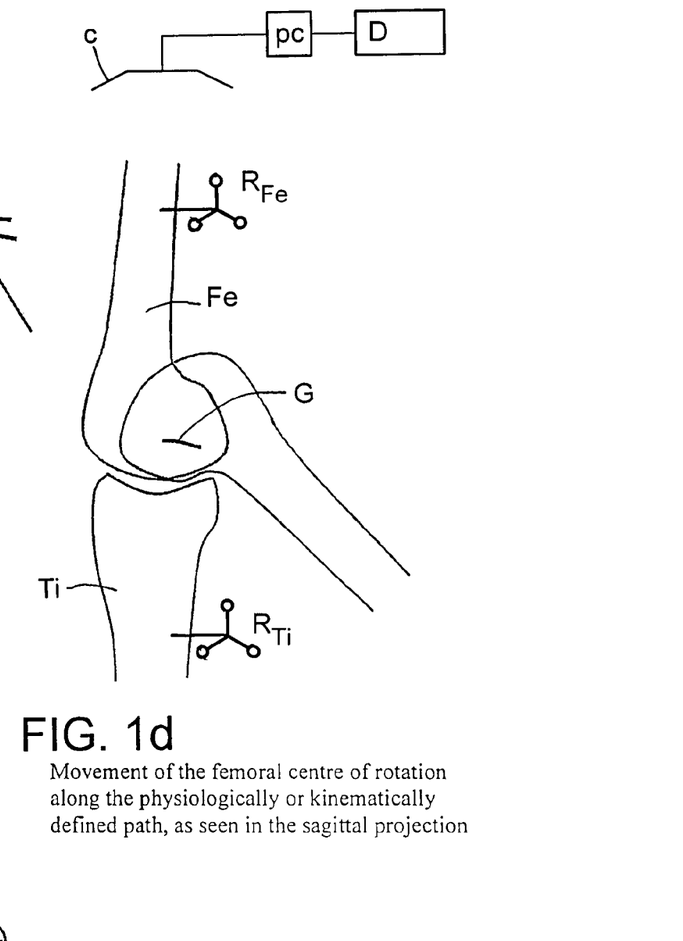

If, for example, a knee joint is viewed in its sagittal, two-dimensional projection (from the side), then the instantaneous axes of rotation passing through the femur (see FIG. 1a) pierce the sagittal plane, as centers of rotation, through the middle of the knee joint (see FIGS. 1b-d).

If the position of the femur with respect to the tibia is tracked, the ascertained centers of rotation of the femur will accordingly lie on or in the vicinity of the moving centrode curve.

If a predefined range is to be used for monitoring the axes of rotation, and this range is for example the moving centrode curve, it can be approximately defined on the one hand by ascertaining the centers of rotation in a range of motion in which there is definitively no collision. According to the model conception by Menschik, the intersecting point of the edges that form the rear and front cruciate ligament in the sagittal projection also corresponds to the instantaneous center of rotation. To define the trajectory of the moving centrode curve using this principle, the intersection point of the connecting lines between the femoral and tibial attachment points can be formed and determined over the mean range of the joint movement that does not lead to a collision of the joint components.

Figure 3A:
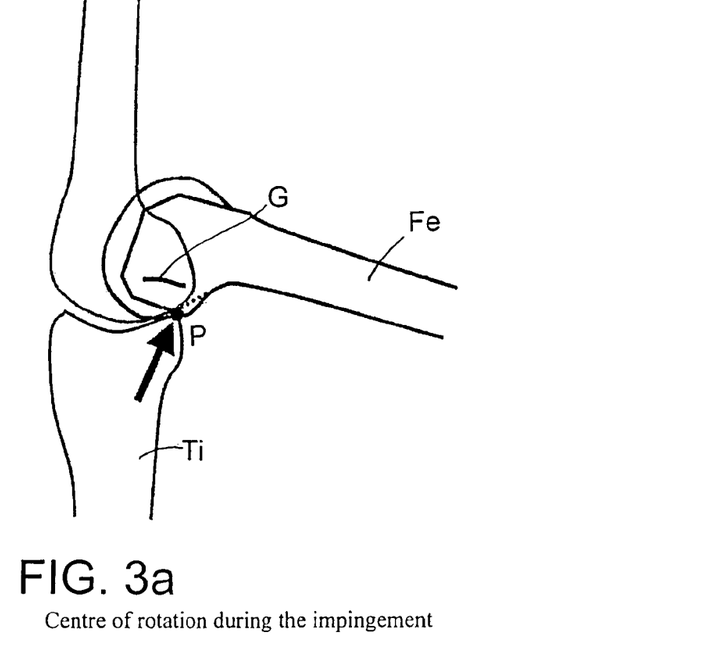
FIGS. 3a and 3b illustrate the shift in the instantaneous axes of rotation in the event of an impingement of the joint components.
Figure 3B:
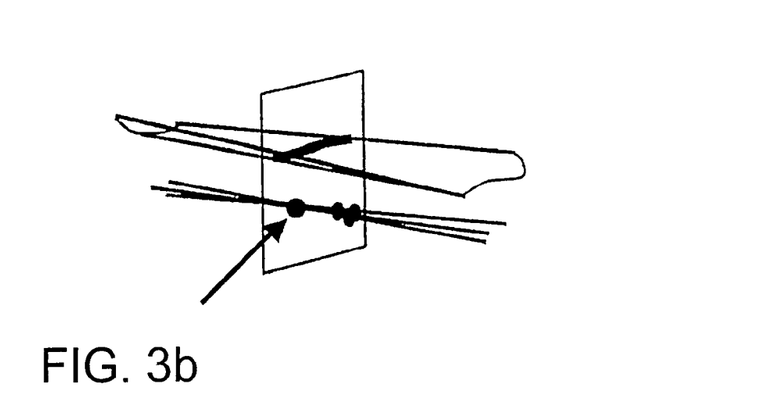
Figure 4:
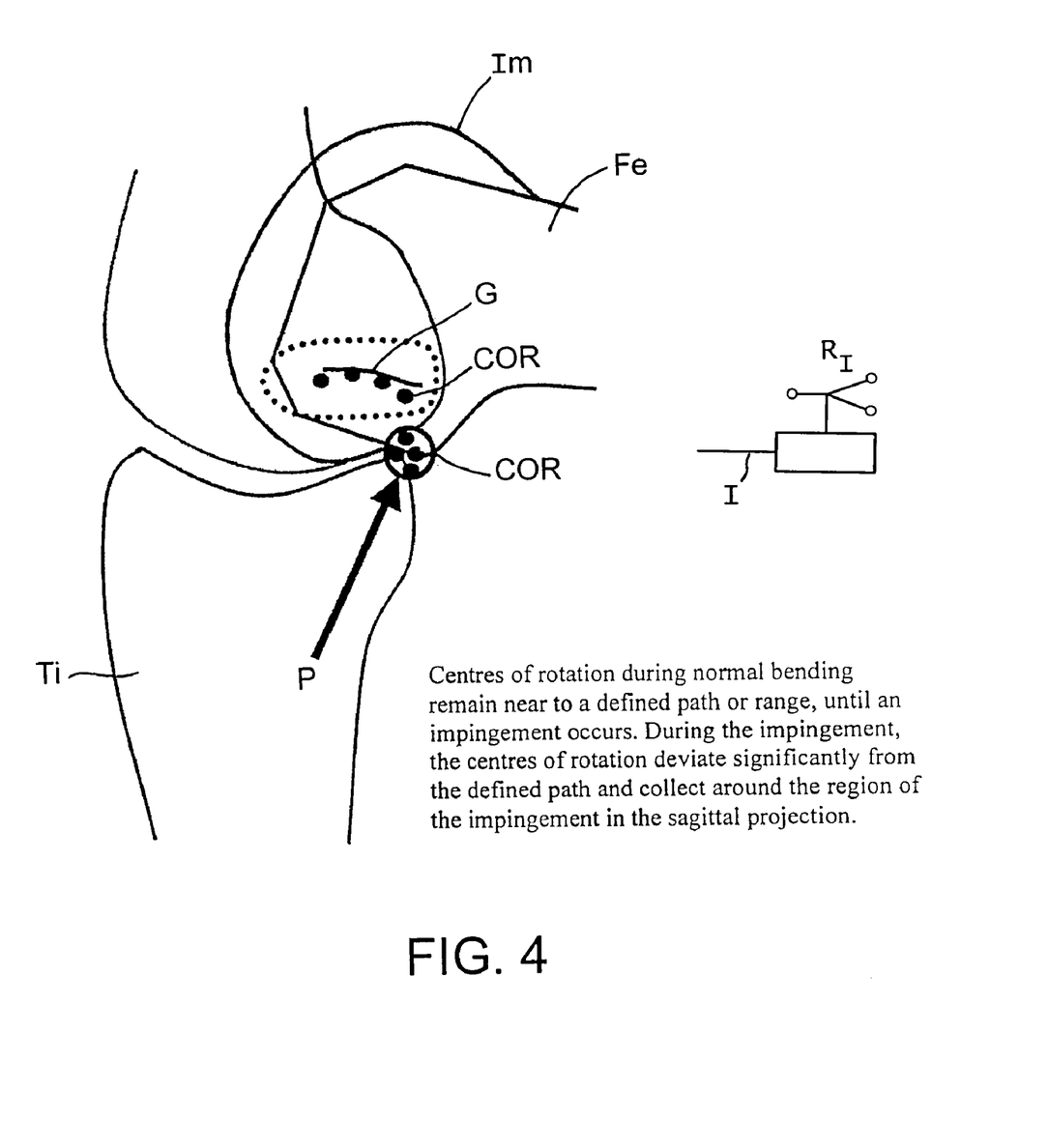

If the calculated, instantaneous, spatially running axes of rotation of the movement or angling of the knee joint starts to deviate from the predefined range (which, in the sagittal projection of the centers of rotation, for example, can be the moving centrode curve) by more than a predetermined distance (e.g., 1 to 50 mm) and approach a posterior part of the tibial plateau and collect at a particular point or delimited or predetermined range, while the angling of the femur is increased, it is very probable that an impingement will occur at this particular point, as shown by the point or range P in FIGS. 3a, 3b and 4. Such impingement can be detected and also localized at the location of the point P when the instantaneous axis of rotation no longer moves in the predefined range but rather jumps to a point or range P. This point or range P can lie on the edge of a functional joint range of one or both joint components provided for the functioning of the joint. This localization can also be performed intra-operatively. Localization can be performed both in the two-dimensional sagittal projection of the centers of rotation, resulting in a point through which the tilting line passes, and spatially by identifying the concentration of the axes of rotation within a narrow spatial range and localizing the point of the impingement or the spatial trajectory of the tilting line in this range.

Figure 2A:
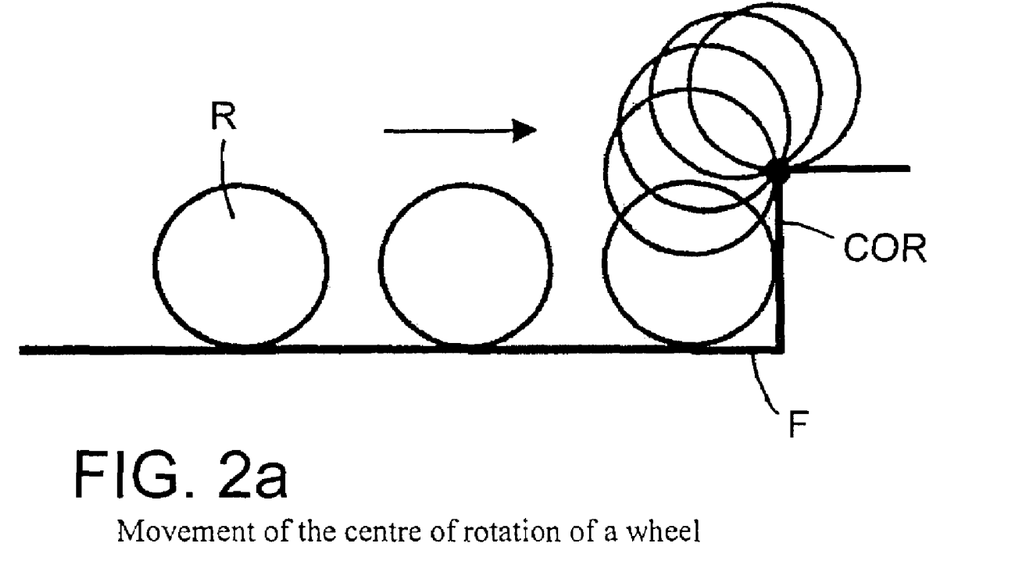
FIGS. 2a and 2b schematically show the movement of an instantaneous center point of rotation during a rolling and tilting movement.
Figure 2B:
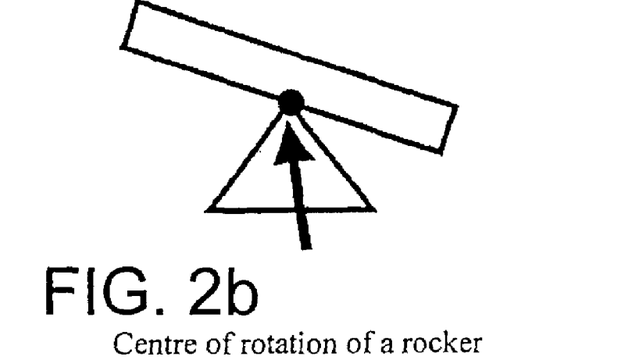

Referring to FIGS. 2a and 2b, the movement of the instantaneous center point of rotation COR of a wheel R rolling off on a bearing area F is shown in the direction of the arrow. It can be seen that the instantaneous center point of rotation COR moves along a straight line level with the base. If, for example, the wheel R comes to a limitation on the area F, such that the wheel R can no longer roll on the area F, then the wheel blocks and, thus, limits the subsequent trajectory of the center point of rotation on the base. If the wheel is moved further upward, it tilts over the bearing point, wherein the new instantaneous center point of rotation no longer moves over the base but is rather concentrated in the region of the bearing point, such that the wheel R, which is no longer rolling off, behaves like a rocker as shown in FIG. 2b. The instantaneous center point of rotation COR always lies on the bearing point highlighted by the arrow.

This knowledge can be utilized in determining the range of motion of an anatomical joint, as schematically shown in FIGS. 1a and 1b. In a similar way to a rocker, the instantaneous center of rotation measured or determined as described herein will be situated at the bearing point P during an impingement and inclination of the joint components or will move relative to it at a small distance (e.g., 0 to 10 mm) as shown in FIG. 3a or FIG. 4. This transition of the instantaneous center of rotation into the collision range can be established by capturing the instantaneous positions of the joint components. A predefined working range, provided for example by the moving centrode curve or other meaningful trajectory, can advantageously be adduced in order to determine whether the joint is still situated within the normal working range, such that if the instantaneous center of rotation deviates from the predetermined range by more than a predetermined distance (e.g., 0 to 20 mm), an impingement can be detected by examining the subsequent trajectory of the center of rotation, localized to the concentration around a point P.

In general, mutually independent measuring methods can be used, which also can be combined in any way, wherein eight criteria or example embodiments are given below:

First, it is possible to observe the deviation of the instantaneous center of rotation (e.g., the piercing points of the axes of rotation in the projection plane) from a predetermined trajectory (e.g., the moving centrode curve) or range. This can be determined, for example, by ascertaining whether the instantaneous center of rotation in the sagittal projection plane (or also in any other suitable orientated projection plane) lies around the predetermined trajectory or range at a predetermined distance (e.g., 5 or 10 mm) as shown by the dotted line in FIG. 4.

Second, it is possible to examine whether at least a predetermined section of the spatially running axis of rotation is situated within a defined volume (e.g., a cuboid, cylinder or sphere) or always intersects a defined area or number of defined areas.

Third, it is possible to ascertain whether the respective change in the position and orientation of the ascertained axis of rotation with respect to any previous determined axis of rotation lies inside or outside predetermined boundaries, for example, in order to establish that the axis has jumped.

The change in position can be tested by defining a limited volume through which one axis passes and in which points of all the other axes to be tested also are situated. The test can be based on each axis and, correspondingly, the volume for each axis can be redefined. The orientation can be tested, for example, by defining two edged areas that are intersected by one axis and wherein both are intersected by each of the other axes. The test can be based on each axis and, correspondingly, the areas for each axis can be redefined.

Fourth, it is possible to ascertain whether the axes of rotation are situated at a defined minimum distance from the surfaces of the joint components (e.g., from the tibia or femur), or from the inserted joint components on the tibia or femur.

Fifth, it is possible to ascertain whether the axis of rotation or center of rotation completely or only partially (see FIG. 2a) covers a predetermined range, in order to be able to establish blocking within the working range and distinguish the blocking from tilting about a collision point.

Sixth, it is possible to ascertain the possible location of the impingement, by iteratively examining the trajectory of the axes of rotation in the region of the impingement on a concentration of the axes of rotation within a delimited volume, as described above. If there are a plurality of common intersecting points or a concentration of the axes of rotation or points of the axes in this volume, or if a partial volume having an accumulation of intersection points is found, then the location of the impingement can be situated in this volume; see FIG. 3b.

Seventh, it is possible to detect the concentration of the centers of rotation in a narrow range in the projection (e.g., the sagittal projection), in order to localize a trajectory of the tilting line through this range.

Eighth, it is possible to test whether the ascertained location or point lies inside or outside a predefined plausibility range, in particular within a joint structure such as for example the femur, in order to rule out incorrect locations. The plausibility range can be a defined area or a volume.

A general movement by a rigid body is composed of a rotation and a longitudinal shift, e.g., a translation, wherein the axis of rotation can shift spatially from moment to moment, such that the direction and location of the instantaneous axis of rotation can change. When considering for example the rolling wheel of a vehicle, it may be established that the instantaneous axis of rotation of the wheel moves with the speed of the vehicle and passes through the point at which the wheel touches the ground.

If the current spatial location of the axis of rotation is sought, the so-called "helical axis" method can be applied.

Based on the Mozzi-Chasles Theorem, which states that any movement of rigid bodies can be resolved into a plane rotation about a suitable axis followed by a translation along the same axis, Rodriguez loc. cit. has described a computational method for determining the underlying movement of rotation and translation from two spatial positions of a body. Panjabi loc. cit. has introduced the method into biomechanics. Woltring loc. cit. proceeds from a transformation matrix. The known rolling movement of a wheel is a special case in which the translation along the instantaneous axis of rotation disappears.

Figure 5:
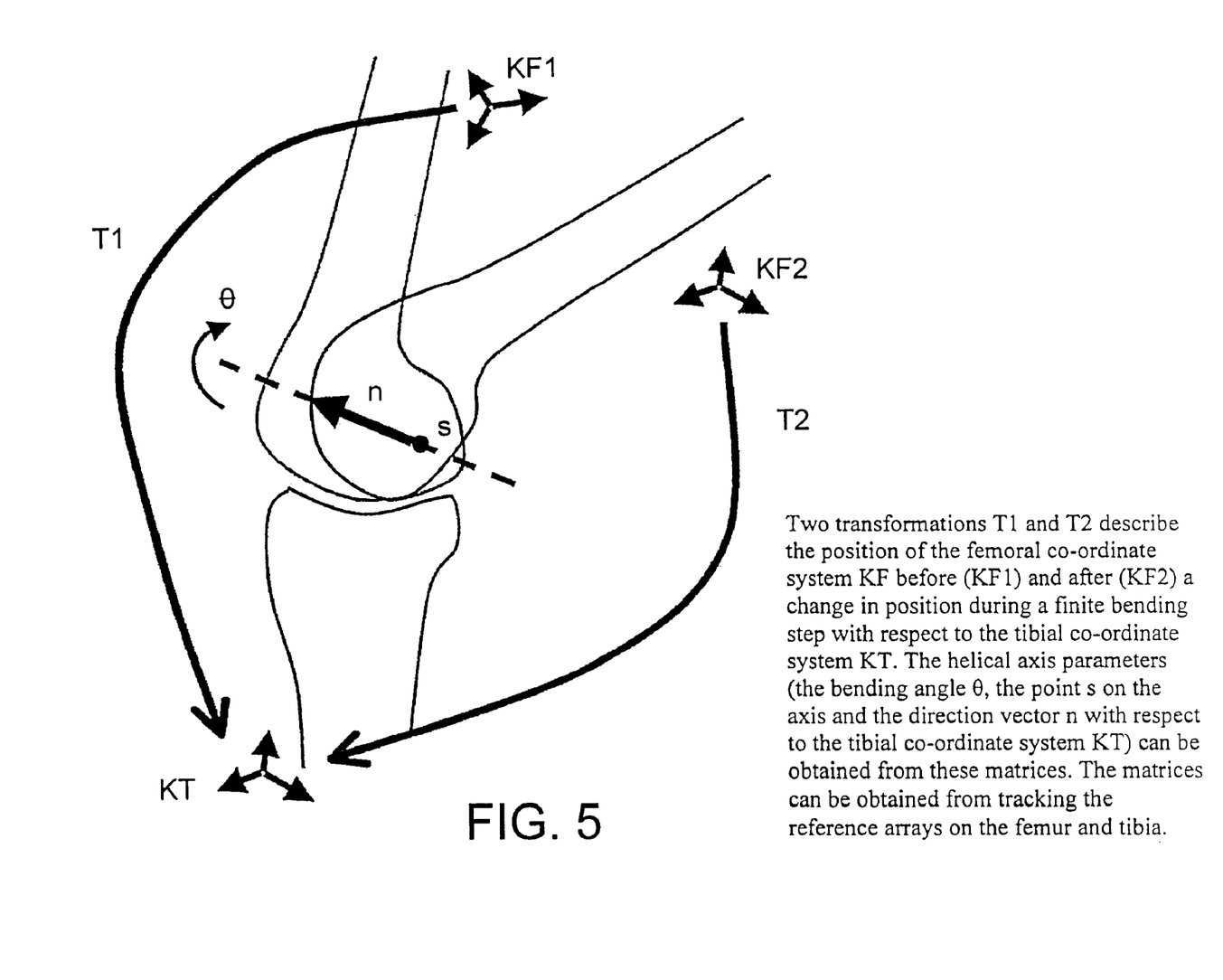
FIG. 5 describes an exemplary method for calculating the instantaneous center point of rotation in accordance with the invention.

The instantaneous axis of rotation can be calculated as explained by FIG. 5. From the transformation matrices T1 and T2, which describe a segment-by-segment change in the position of the reference star connected to the femur during an angling (flexion) of the joint with respect to the tibia, it is possible to obtain the finite axis of rotation (as a helical axis) having the direction vector n and a point S in coordinates of the tibial system, and the magnitude of the rotation $\theta$. For details of the calculation which is as insusceptible to faults as possible, see Woltring loc. cit. By resolving the overall movement of the joint into a sequence of such small changes in position, it is possible to determine the trajectory of the axis of rotation segment-by-segment. The method can be performed every time a movement is completed.

It is thus possible to detect the impingement of components of an anatomical joint by examining the cited criteria. The location of the impingement lies on the instantaneous axis of rotation. If it is established that an impingement does not occur during the movement of the joint over the desired range of motion, it is not necessary to trim joint components of an anatomical joint as is otherwise usual. This retains healthy body tissue and saves time. If it is ascertained where an impingement of the joint components is occurring, a surgeon can correspondingly change the joint components and, for example, trim points or areas responsible for the undesirable impingement so as to effectively eliminate the impingement of the joint components (and therefore the restriction of the range of motion).

A surgical instrument that is moved, for example, in order to cut a joint component, such as the condyles, can preferably be navigated to the location of the impingement, which can be ascertained as described herein. This is advantageous in minimally invasive methods, in which a free view onto the joint is not generally obtainable.

It is thus possible to reliably ascertain the maximum range of motion before any further physiological limitations or damage, for example, to the cruciate ligaments occur.

Also described herein is a computer program which, when it is running on a computer or is loaded onto a computer, performs one or more of the method steps described above, and to a program storage medium or computer program product comprising such a computer program.

A device for performing the methods described herein comprises at least one capturing unit which can capture the spatial position of reference arrays attached to joint components. This capturing unit, such as for example an infrared camera, may be operatively coupled to a computer that can calculate an instantaneous axis of rotation, instantaneous center point of rotation, or center of rotation of the joint components, moved relative to each other and connected by a joint, from the captured positions of the reference arrays connected to the joint components. The computer can further establish whether the instantaneous points of rotation move along a curve to be interpolated having a defined maximum curvature radius and exceed or do not exceed a given minimum distance from the curve or from each other, or whether the instantaneous axes of rotation cover a spatial area to be interpolated having a defined maximum curvature and exceed or do not exceed a given minimum distance from the spatial area and/or whether the change in orientation of the axial vector between the axes exceeds or does not exceed a defined maximum angle, or whether there is a jump in the recalculated center point of rotation or the recalculated instantaneous axis of rotation at a particular angled state of a joint component, such that an impingement of the joint components can be deduced and the location or range of the impingement can also be localized. The computer can equally establish whether the instantaneous points of rotation move along a constant straight line, whether instantaneous axes of rotation lie on a spatial area, or whether they move along a curve. Further, the computer can establish whether there is an inconsistent jump in the recalculated center point of rotation or the recalculated instantaneous axis of rotation at a particular angled state of a joint component, such that an impingement of the joint components can be deduced and the location or range of the impingement can also be localized.

In addition or alternatively, one or more of the eight criteria described by way of example above can equally be used.

The computer is preferably connected to a database in which for example information regarding the three-dimensional geometry of the joint components, such as for example the femur and/or the tibia or joint implants, is stored. Furthermore, the trajectory of a curve, area or volume (e.g., the moving centrode curve relative to the tibia or the locked centrode curve relative to the femur) can also be stored in the database. The data regarding the three-dimensional structure of the joint components or regarding the trajectory of the centers of rotations (for example a moving centrode curve) can be obtained or predetermined before examining the range of motion, for example by means of a computer tomograph or a preceding movement analysis.

BRIEF DESCRIPTION OF THE DRAWINGS

The forgoing and other features of the invention are hereinafter discussed with reference to the drawing.

FIG. 4 is a detailed representation of FIG. 3a.

DETAILED DESCRIPTION

FIG. 1d shows a knee joint, wherein a reference star $R_{Ti}$ is fastened to the tibia Ti. Above the tibia Ti is the femur Fe which is shown in two differently angled positions relative to the tibia Ti and is connected to a reference star $R_{Fe}$. A computer PC is operatively coupled to a database D and to a camera C. Movement of the femur Fe can be detected by the camera C, which in turn can provide such data to the computer PC. The computer PC can calculate or otherwise determine the instantaneous center point of rotation of the femur Fe along the moving centrode curve G.

If an impingement occurs between the femur Fe and the tibia Ti, as shown in FIGS. 3a and 4, then the femur Fe and the tibia Ti come into contact at the point P, such that the new center point of rotation calculated by the computer PC from the positional data of the markers $R_{Fe}$ and $R_{Ti}$ is no longer a constant continuation of the curve G, but rather jumps to a location on the tibia Ti. If, for example, the dimensions of the implant Im (FIG. 4) placed onto the femur Fe are known, then a part of the tibia Ti can be trimmed by a surgeon. For example, the surgeon can use an instrument I provided with a reference star $R_I$, wherein the instrument is navigated to the point P so as to trim the tibia Ti.

FIG. 4 shows the instantaneous center points of rotation COR, calculated by means of the computer PC, during a normal bending or angling of the joint. The instantaneous center points of rotation COR move in the vicinity of the moving centrode curve G until an impingement occurs. During the impingement, the instantaneous center points of rotation COR calculated by the computer PC deviate significantly from the predetermined curve, for example the moving centrode curve G, and collect in the region of the contact point P.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for detecting an impingement of at least two joint components of a joint, comprising:
    detecting, via a medical tracking system, a spatial position of the at least two joint components during a relative movement of the at least two joint components;
    calculating, with computer assistance, an instantaneous center point of rotation or an instantaneous axis of rotation from the detected spatial positions of the at least two joint components;
    when a first joint component of the at least two joint components is moved relative to a second joint component of the at least two joint components, establishing whether the calculated instantaneous center point of rotation moves within a first expectation range or whether the calculated instantaneous axis of rotation moves within a second expectation range;
    concluding that there is an impingement of the at least two joint components when at least one of the calculated instantaneous center point of rotation or the calculated instantaneous axis of rotation deviates from the respective expectation range; and
    providing an output indicative of whether or not there is an impingement of the at least two joint components.

2. The method according to claim 1, wherein deviating from the respective expectation range includes deviating from a constant line or curved area.

3. The method according to claim 1, wherein establishing whether the calculated instantaneous center point of rotation moves within the first expectation range includes the first expectation range being along a constant line.

4. The method according to claim 3, wherein establishing whether the calculated instantaneous axis of rotation moves within the second expectation range includes the second expectation range being a curved area.

5. A method for detecting an impingement of at least two joint components of a joint, comprising:
    detecting, via a medical tracking system, a spatial position of the at least two joint components during a relative movement of the at least two joint components; calculating, with computer assistance, an instantaneous center point of rotation or an instantaneous axis of rotation from the detected spatial positions of the at least two joint components;
    when a first joint component of the at least two joint components is moved relative to a second joint component of the at least two joint components, determining at least one of
        a) whether at least a predetermined section of a spatially running axis of rotation is situated within a defined volume or moves over a defined area,
        b) whether a position or orientation of the calculated axis of rotation relative to a joint component of the at least two joint components or a previously determined axis of rotation lies within predetermined boundaries, or
        c) whether a concentration of axes of rotation or points of the axes of rotation lie within a predetermined volume; and outputting a result of the determination.

6. The method according to claim 5, wherein determining whether the concentration of axes of rotation or points of the axes of rotation lie within the predetermined volume includes using a cuboid, cylinder or sphere as the predetermined volume.

7. The method according to claim 1, further comprising performing a movement analysis to calculate the instantaneous center point of rotation.

8. The method according to claim 1, further comprising at least one of:
    localizing a point of the impingement or a range of the impingement relative to the first and/or second joint component; and
    detecting a concentration of the center of rotation in a range in order to localize the point or a trajectory of a tilting line.

9. The method according to claim 8, further comprising testing whether the ascertained point of impingement or range of impingement lies inside or outside a predetermined range to rule out incorrect locations.

10. The method according to claim 9, wherein the predetermined range is a defined area or a volume.

11. The method according to claim 9, wherein the predetermined range lies within a joint structure.

12. The method according to claim 8, further comprising navigating an instrument to the localized impingement point.

13. The method according to claim 1, further comprising establishing whether the axis of rotation or center of rotation completely or only partially covers a predetermined range so as to establish blocking within a working range of the at least two joint components and distinguishing such blocking from tilting about a collision point.

14. The method according to claim 1, wherein concluding that there is an impingement of the at least two joint components when the calculated instantaneous center point of rotation deviates from the respective expectation range includes detecting impingement when the instantaneous center points of rotation deviate from a predetermined curve by a predetermined value.

15. The method according to claim 14, wherein the predetermined curve is a moving centrode curve.

16. The method according to claim 1, further comprising using three-dimensional models of the at least two joint components and/or of implants to determine if a joint component of the at least two joint components is approaching another joint component of the at least two joint components.

17. The method according to claim 1, wherein an impingement is detected when the joint is moved and instantaneous center points of rotation do not substantially move along a line or move along a curve and pass through curved segments having gaps or curvatures above predetermined boundary values.

18. The method according to claim 1, further comprising obtaining positional data from a reference array attached to at least one joint component of the at least two joint components.

19. The method according to claim 18, wherein the positional data is obtained using at least one of an optical, electromagnetic or mechanical position capturing system or tracking system.

20. The method according to claim 1, wherein a maximum range of motion of the joint is determined as the range between the impingements of the first and second joint components during a movement from one maximum joint excursion to another maximum joint excursion.

21. A computer readable medium comprising computer executable instructions adapted to detect an impingement of at least two joint components of a joint,
wherein a spatial position of each joint component of the joint is detected by a medical tracking system during a relative movement of the joint components, comprising:
code configured to calculate an instantaneous center point of rotation or an instantaneous axis of rotation from the detected spatial positions of the joint components;
when a first joint component of the at least two joint components is moved relative to a second joint component of the at least two joint components, code configured to establish whether the calculated instantaneous center point of rotation moves within a first expectation range or whether the calculated instantaneous axis of rotation moves within a second expectation range;
code configured to conclude that there is an impingement of the at least two joint components when at least one of the calculated instantaneous center point of rotation or the calculated instantaneous axis of rotation deviates from the respective expectation range; and
code configured to output whether or not there is an impingement of the at least two joint components.

* * * * *